United States Patent [19]

Ash

[11] Patent Number: 5,322,519
[45] Date of Patent: Jun. 21, 1994

[54] FOLDABLE CATHETER FOR PERITONEAL DIALYSIS

[75] Inventor: Stephen R. Ash, West Lafayette, Ind.

[73] Assignee: Ash Medical Systems, Inc., West Lafayette, Ind.

[21] Appl. No.: 19,367

[22] Filed: Feb. 17, 1993

[51] Int. Cl.⁵ ............................................. A61M 25/00
[52] U.S. Cl. .................................... 604/264; 604/280
[58] Field of Search ............... 604/175, 264, 280, 283, 604/284

[56] References Cited

U.S. PATENT DOCUMENTS

| | | | |
|---|---|---|---|
| 4,256,102 | 3/1981 | Monaco | 604/280 |
| 4,368,737 | 1/1983 | Ash | 604/175 |
| 4,398,910 | 8/1983 | Blake et al. | |
| 4,929,236 | 5/1990 | Sampson | 604/175 |

OTHER PUBLICATIONS

Ash et al., Dialysis and Transplantation 10(5):383–386 (1981).
Handt et al., Perspectives in Peritoneal Dialysis 2(3):30–33 (1984).
"How to Use the Y-TEC System", published by Janingroup, Inc. (1988).

*Primary Examiner*—Jerome L. Kruter
*Attorney, Agent, or Firm*—Olson & Hierl, Ltd.

[57] ABSTRACT

A foldable peritoneal catheter is provided with a flexible central plenum chamber and flexible fluted wands or rods that extend outwardly from the plenum chamber and serve as liquid transport means for a dialysate fluid or the like. This type of peritoneal catheter is well suited for chronic peritoneal dialysis.

11 Claims, 2 Drawing Sheets

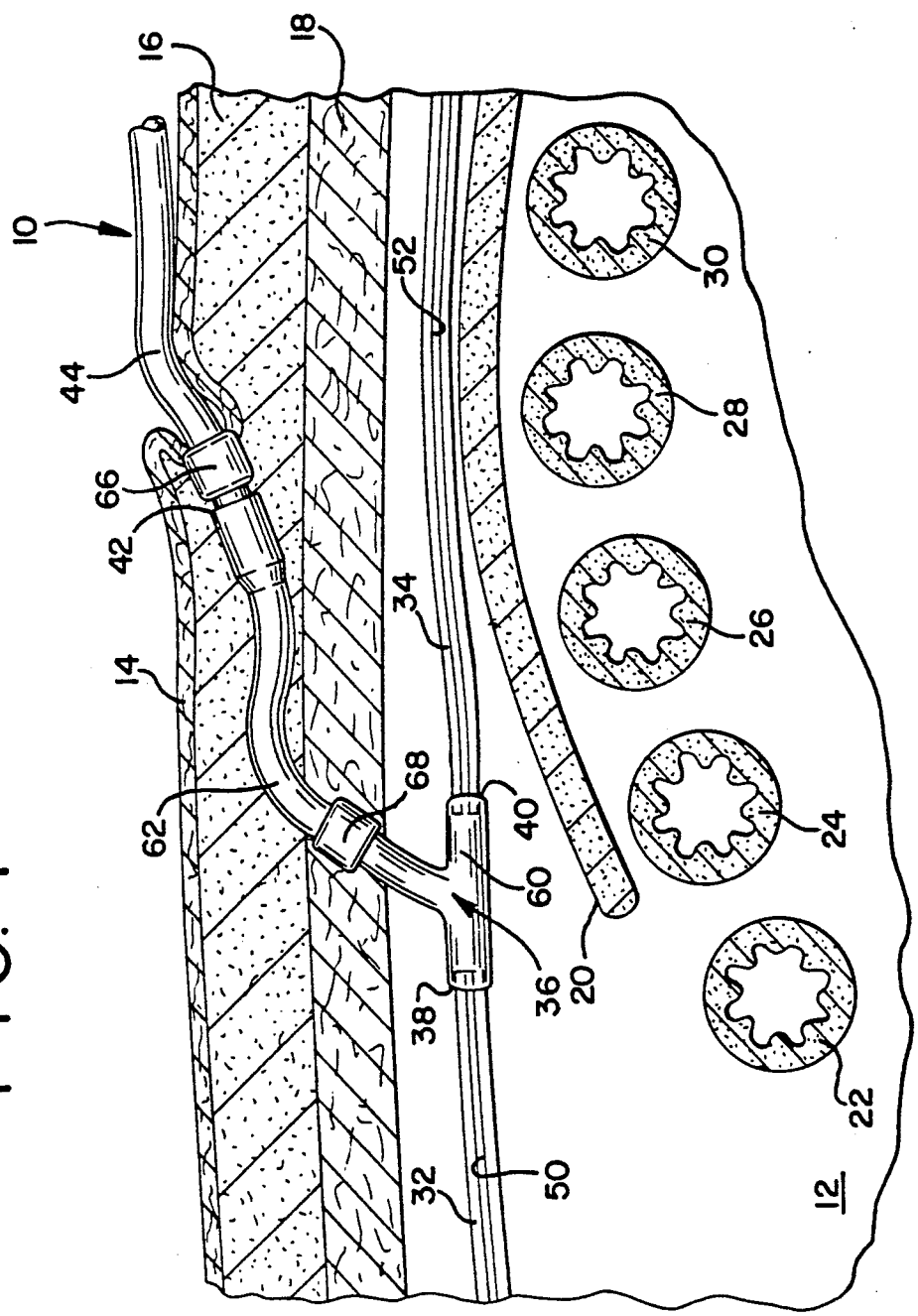
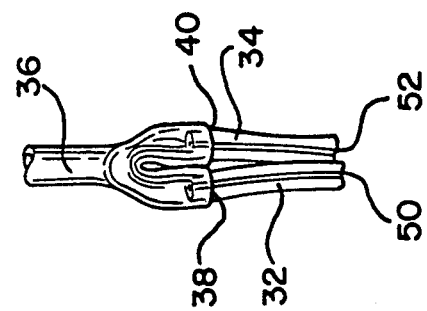

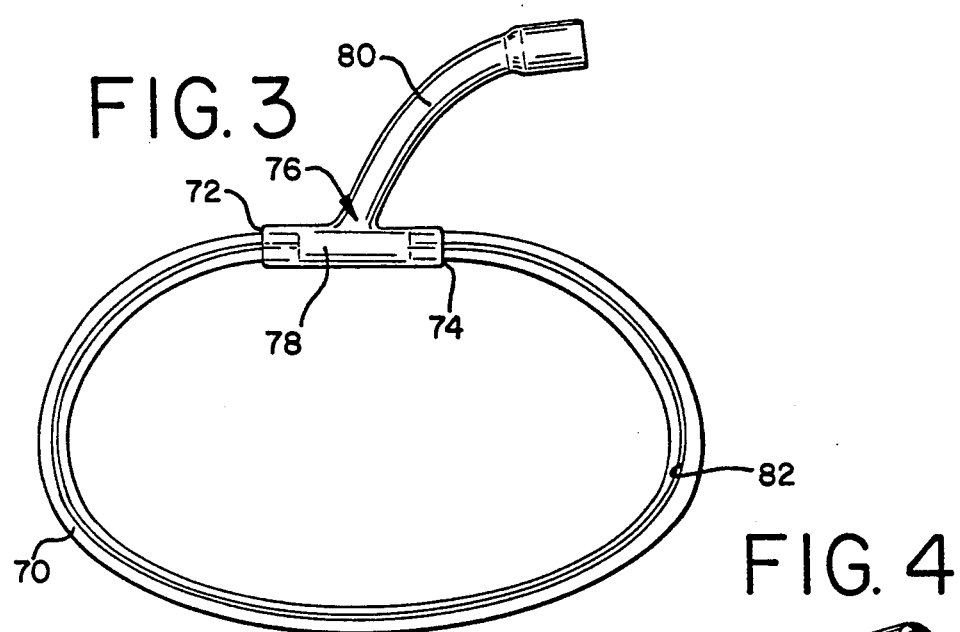
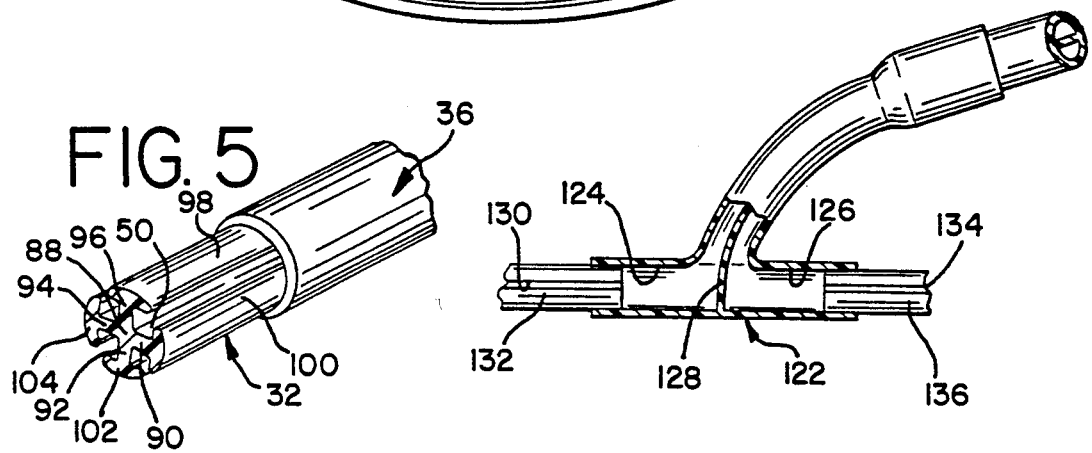
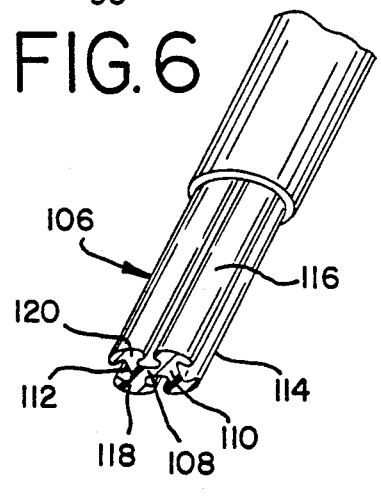
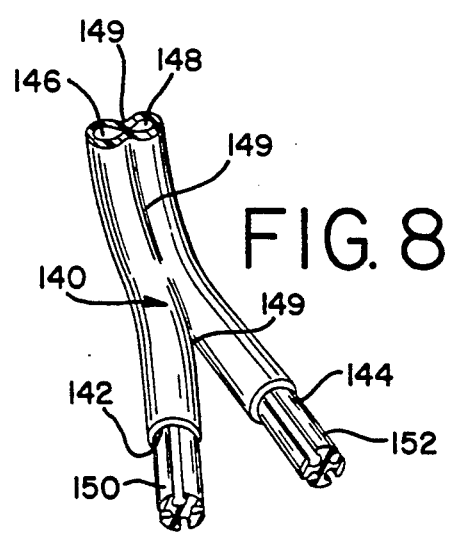
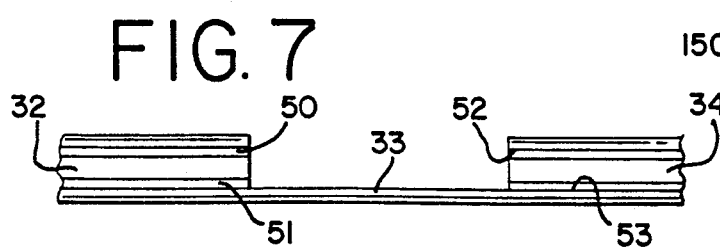

5,322,519

FOLDABLE CATHETER FOR PERITONEAL DIALYSIS

TECHNICAL FIELD

This invention relates to catheters well suited for use in peritoneal dialysis.

BACKGROUND OF THE INVENTION

Peritoneal dialysis catheters are of two general types: those designed for acute use (three days or less) and those for chronic use (over three days). Acute peritoneal dialysis catheters are straight, relatively rigid nylon or polyethylene catheters with numerous perforations or sideholes on the intraperitoneal portion. Chronic peritoneal dialysis catheters are constructed of soft materials like silicone rubber or polyurethane. The intraperitoneal portion may contain sideholes like the acute catheter, but may also have larger apertures for passage of the peritoneal fluid. Some chronic catheters have disks, beads or flanges at the parietal peritoneum to fix the catheter position. All have one or two extraperitoneal cuffs, which promote a local inflammatory response and tissue ingrowth, producing a fibrous plug to fix the catheter in position, prevent fluid leaks, and prevent bacterial migration around the catheter.

Some acute catheters are advanced into the abdomen with a pointed metal stylet inside; others have a tapered tip and are advanced into the abdomen over a guidewire. Acute catheters are fixed in place by suturing wings to the skin surface. Since there is no barrier to bacterial migration around the catheter, and because of the stiffness of the catheter, there is a significant risk of peritonitis, peritoneal irritation, and bowel perforation if the catheter is left in place for more than three days. For patients with acute renal failure, therapy usually is necessary for much more than three days. For these patients, safer access is provided by placing a chronic catheter at the start of dialysis therapy.

Historically, chronic peritoneal catheters have been made from a hydrophobic silicone polymer. However, such catheters suffer from a variety of problems such as infection of the biofilm on the catheter with attendant recurrent peritonitis, omental attachment to the catheter with resulting outflow obstruction, as well as mechanical failures leading to detachment of the catheter connectors.

Recently, curled peritoneal catheters have been made from a hydrophilic polyurethane. While this material of construction usually is smoother and stronger than a silicone polymer of comparable dimensions, such hydrophilic polyurethane catheters have not exhibited a reduced incidence of recurrent peritonitis, outflow obstruction or mechanical failures.

SUMMARY OF THE INVENTION

The present invention provides a foldable catheter that is eminently well suited for peritoneal dialysis.

In particular, the present catheter includes a resilient, foldable housing, usually of a T-shaped or Y-shaped configuration, from which extend plural flexible fluted rods or wands having channels that gather or distribute a liquid such as a dialysis fluid. The foldable housing defines a plenum chamber for the liquid and at least three access ports to the plenum chamber. An elongated, flexible, fluted, virgate liquid transport segment is received in and extends outwardly from each of two of the access ports. The third access port can serve for introducing a liquid into the plenum chamber for further distribution by the fluted liquid transport segments, or it can also serve for withdrawing from the plenum chamber a liquid conveyed to the plenum chamber along the fluted liquid transport segments.

BRIEF DESCRIPTION OF THE DRAWINGS

In the drawings,

FIG. 1 is a schematic, elevational fragmentary view showing a catheter embodying the present invention and positioned within the peritoneal cavity of a patient;

FIG. 2 is a fragmentary view showing the present catheter in a folded configuration for introduction into a patient;

FIG. 3 is a fragmentary view showing an embodiment of the present invention wherein the end portions of a single liquid transport segment are received into a foldable housing that serves as a plenum chamber;

FIG. 4 is a fragmentary view, partially broken away to show interior detail, illustrating an alternate embodiment of the present invention in which the plenum chamber is partitioned by a septum;

FIG. 5 is a fragmentary perspective view, partly in section, illustrating a type of flexible fluted rod or wand that can be utilized in conjunction with the foldable housing;

FIG. 6 is a fragmentary perspective view, partly in section and illustrating another type of flexible fluted rod or wand that can be utilized in conjunction with the foldable housing;

FIG. 7 is a fragmentary view illustrating two interconnected fluted rods or wands; and FIG. 8 is a fragmentary perspective view illustrating a foldable housing in a Y-configuration and having an internal septum that partitions the housing.

DESCRIPTION OF PREFERRED EMBODIMENTS

Catheters embodying the present invention are relatively compact and foldable, and are particularly well suited for chronic use, i.e., for time periods in excess of three days. As such, these catheters can be readily positioned within the peritoneal cavity and minimize several shortcomings of currently available peritoneal dialysis catheters, to wit, outflow obstruction due to omental attachment, subcutaneous leaks, extrusion of the catheter leading to pericatheter hernias, exit site erosion, and the like. Suitable materials of construction for the present catheters are physiologically compatible, relatively soft materials such as silicone rubber, flexible polyurethanes, and the like.

Referring to the drawings, FIG. 1 schematically shows a fluted peritoneal dialysis catheter 10 situated within peritoneal cavity 12. Fluted catheter 10 passes through epidermis 14, across subcutaneous tissue 16, and through abdominal wall 18. Omentum 20 overlies bowel loops 22, 24, 26, 28 and 30.

A pair of fluted, virgate (i.e., rod- or wand-shaped) liquid transport segments 32 and 34 extend outwardly from a flexible, foldable and resilient housing 36 that defines a plenum chamber with at least three access ports such as ports 38, 40 and 42. The fluted, virgate segments 32 and 34 are received at one end within housing 36 and extend outwardly from respective ports 38 and 40. Port 42 is in fluid communication with the distal end portion of transcutaneous inflow/outflow tube 44 which tube, in turn, externally is in fluid communication with an appropriate dialysate source. It has been found that the omentum is not likely to attach to the longitudinal flutes (channels or grooves) of the liquid transport segments, thus dialysate outflow and inflow obstruction problems experienced with perforated peritoneal dialysis catheters are avoided. Each of the liquid transport segments, such as segments 32 and 34, are about 5 to about 15 centimeters long, preferably about 10 to about 12 centimeters long.

Each fluted, virgate segment, such as segments 32 and 34 is flexible and is provided with straight flutes defining plural liquid transport channels along the surface of the segments of which channels 50 and 52 are illustrative. The liquid transport channels extend along the longitudinal axes of segments 32 and 34, preferably along the entire length of each liquid transport segment.

In the embodiment shown in FIG. 5, the fluted liquid transport segment 32 has a substantially cylindrical configuration and a circular cross-sectional contour normal to its longitudinal axis. Segment 32 comprises a core portion 88 with four peripherally spaced struts 90, 92, 94 and 96 extending radially outwardly from core portion 88. At the outer ends thereof the struts terminate in overhang portions 98, 100, 102 and 104 that are coextensive in length with the struts.

In an alternative embodiment shown in FIG. 6, a fluted segment 106 having an oval or ovoid cross-sectional contour normal to its longitudinal axis is provided with core portion 108 and substantially parallel struts 110 and 112 that are unitary with core portion 108 and together with core portion 108 define plural liquid transport channels. Each of the struts terminates in two overhang portions, i.e., overhang portions 114 and 116 for strut 110 and overhang portions 118 and 120 for strut 112. If desired, the longitudinal edge portions of each overhang portion can be made relatively thin and overlapping so as to define patulous liquid transport channels for the inflow side of a continuous peritoneal dialysis system. Such channels are normally closed but can be spread open by the dynamic liquid head or pressure of the inflowing dialysate.

The fluted segments preferably have a diameter of about 5 millimeters (15 French). The slots or channels, such as channels 50 and 52 in segments 32 and 34, preferably have a width of about 1 millimeter.

Preferably, the segments received in a flexible housing, such as segments 32 and 34 in housing 36, are connected to one another in order to minimize the likelihood that one or both of the fluted segments becomes separated from the housing while the catheter is implanted in the patient or upon withdrawal of the catheter from the patient. To that end, segments such as segment 32 with liquid transport channels 50 and 51 and segment 34 with liquid transport channels 52 and 53 can be joined to one another by a flexible link such as coupling 33 shown in FIG. 7. Coupling 33 is unitary with segment 32 as well as with segment 34. Such a flexible link can be readily made by cutting away, in a selected region of a fluted strip, its central core portion, the struts associated therewith and all but one of the overhang portions. The remaining overhang portion then serves as a unitary link between two fluted segments that can be threaded through two of the access ports in the flexible housing.

Housing 36 is foldable and flexible, as well as resilient, so that it can be temporarily linearized to pass through a Quill® catheter guide normally used during peritoneoscopic catheter placement, or through split sheaths normally utilized during blind catheter placement. Once placed within the peritoneal cavity, housing 36 unfolds and returns substantially to the original configuration thereof.

Housing 36 in a folded configuration is illustrated in FIG. 2.

The Quill® catheter guide is well known in the art and is described, inter alia, in Handt & Ash, Perspectives in Peritoneal Dialysis 2(3):30-33 (September 1984). A preferred catheter placement procedure will be described in greater detail hereinbelow.

As shown in FIG. 1, the flexible and foldable housing 36 of a T-fluted catheter embodying the present invention is hollow and has a substantially T-shaped configuration. The cross-limb 60 of the "T" is hollow and fixes the position of the catheter against extrusion when in place. The transabdominal limb 62 is also hollow and preferably is molded in a curved or arcuate configuration that permits this particular portion of housing 36 to conform to the abdominal wall 18 as well as subcutaneous tissue 16 thickness of the patient, whether obese or thin. More preferably, the transabdominal limb includes an arcuate portion of about $\pi/2$ radians and having a substantially constant radius of curvature.

At the juncture of the transabdominal limb 62 and the cross limb 60, flexible housing 36 provides an articular junction which can have a generally T-shaped lobate contour as shown in FIG. 1, a generally Y-shaped contour as illustrated in FIG. 8, as well as an orbiculate contour, e.g., spheroid, ovoid, bursiform, that facilitates articulation at the aforesaid junction, and thus promotes passage through a catheter guide while in a folded configuration. The flexible housing 36 can also be provided with pleats that permit relatively compact folding of housing 36 during catheter placement.

Subcutaneous cuff 66 and deep cuff 68 are of conventional design, usually made of a fibrous polyester (e.g., Dacron®). These cuffs promote the ingrowth of tissue when used on chronic catheters, and thus assist in anchoring the catheter as well as preventing infection. It is preferred to use at least two cuffs, spaced from one another, to further increase the region for ingrowth of tissue.

In another embodiment, illustrated in FIG. 3, opposite end portions of the same fluted segment 70 are received in juxtaposed access ports 72 and 74 of T-shaped foldable housing 76. Cross-limb 78 and curved transabdominal limb or stem 80 of housing 76 together define a plenum chamber for the distribution of the dialysis liquid along channels or grooves 82 in liquid transport segment 70. One or more cuffs can be provided on transabdominal limb 80 as desired.

For a continuous peritoneal dialysis system the dialysate inflow pathway and the dialysate outflow pathway must be separate. One such arrangement is illustrated in FIG. 4 where flexible housing 122 is partitioned into two adjacent plenum chambers 124 and 126 by septum 128. Plenum chamber 124 communicates with the channels such as channel 130 defined by fluted segment 132. Similarly, plenum chamber 126 communicates with the channels such as channel 134 defined by fluted segment 136. One of the plenum chambers, e.g., chamber 124, serves to distribute the inflowing dialysate among the channels in fluted segment 132 while the other plenum chamber, chamber 126, serves to gather spent dialysate that enters this plenum chamber via the channels such as channel 134 in fluted segment 136.

Another embodiment suitable for continuous peritoneal dialysis is illustrated in FIG. 8 where a Y-fluted peritoneal dialysis catheter is shown. Flexible and foldable housing 140 is a substantially Y-shaped dual lumen housing and defines access ports 142 and 144 as well as access ports 146 and 148. Each of access ports 142 and 144 receives, respectively, one end of fluted liquid transport segments 150 and 152. Septum 149 along with housing 140 defines a pair of adjacent plenum chambers and separates a passageway communicating with ports 142 and 146 from a passageway communicating with ports 144 and 148.

The number of channels and their sizes are selected to minimize hydraulic resistance while providing a dialysate flow rate in the range of about 100 milliliters/minute to about 500 milliliters/minute, preferably about 200 milliliters/minute. For continuous flow peritoneal dialysis the dialysate flow rates are in the range of about 25 milliliters/minute to about 200 milliliters/minute. The channels in the fluted segments of the peritoneal catheter are sized accordingly. Moreover, for a continuous peritoneal dialysis catheter, the channels on the dialysate outflow side can have a relatively greater volumetric capacity than the channels on the inflow side so as to accommodate the liquid volume removed during dialysis.

Placement of the present peritoneal catheters can be readily effected using a Quill ® catheter guide or a similar longitudinally slit tubular guide. Specifically, in one particular placement procedure, a 2-cm incision is made under local anesthesia, and a cannula and trocar are placed in the abdomen, the longitudinally slit Quill ® catheter guide having been attached by its pointed tip to the cannula;

the trocar is removed, a 2.2-mm peritoneoscope is placed through the cannula to assure intraperitoneal location of the tip, the scope is removed, about 600 cc of air is infused, and the scope reinserted;

the cannula is directed, under vision, into a clear space within the abdomen, then the scope and cannula are removed, leaving the Quill ® guide in the direction chosen for the catheter in the peritoneum;

the Quill ® guide is dilated with 3-mm and 5-mm diameter plastic rods, opening the guide laterally to expand the abdominal wall;

a catheter, such as the T-fluted catheter, provided with a deep cuff and a subcutaneous cuff, is folded and placed within a SECOND Quill ® guide, with the two fluted segments forward and the Quill ® guide forming a tapered chamber around the segments and the folded T-shaped housing;

the second Quill ® guide is inserted upside-down into the first Quill ® guide, with the opening of the second guide facing the closed portion of the first guide;

the second Quill ® guide is advanced into the abdomen until a decreasing resistance signifies that the T-shaped housing has entered the abdomen;

the first (outer) Quill ® guide is removed over the second (inner) Quill ® guide;

using a plastic rod dilator, the T-shaped housing is expelled from the second Quill ® guide through the slot on the side of this guide;

the second Quill ® guide is removed, leaving the T shaped housing against the parietal (outer) peritoneum, and the catheter's deep cuff within the musculature, without placement of abdominal sutures; and the transabdominal limb of the T-shaped housing and the distal end of the inflow/outflow tube connected thereto are tunneled below the skin to a separate exit site, leaving the subcutaneous cuff about 2 cm from the exit. The patient's wound is then closed in accordance with standard catheter placement techniques.

Alternatively, catheter placement can be effected with a single Quill ® catheter guide, or a similar longitudinally-slit catheter guide, as follows.

Subsequent to the insertion of the first catheter guide as described hereinabove, the fluted liquid transport segments of the peritoneal catheter are aligned within the catheter guide and the caudally-directed, leading fluted liquid transport segment is advanced into the peritoneal cavity along the guide and using a hemostat or the like implement. During this procedure, when the plenum chamber portion of the catheter is at about the abdominal wall, the trailing fluted liquid transport segment is folded within the catheter guide and under the plenum chamber portion, and similarly advanced into the peritoneal cavity, ultimately folding over itself the plenum chamber.

At about this stage of the placement procedure the leading liquid transport segment and the adjacent plenum chamber portion exit from the catheter guide into the peritoneal cavity and begin to rest against the parietal peritoneum. Next the limb of the flexible catheter housing that carries the deep cuff, the transabdominal limb, is positioned within the catheter guide and advanced toward the peritoneal cavity so as to position the deep cuff substantially as shown in FIG. 1.

Thereafter, the tubular catheter guide is withdrawn while the inserted catheter is maintained in position. A tunnel is made in the subcutaneous tissue toward the skin exit site to accommodate the transabdominal limb. An external catheter is connected to the transabdominal limb and the patient's wound is closed in accordance with standard catheter placement techniques.

The foregoing description and the accompanying drawings are intended as illustrative but not limiting. Still other variations and rearrangements of parts are possible without departing from the spirit and scope of the present invention.

I claim:

1. A catheter suitable for peritoneal dialysis and comprising a resilient, foldable housing defining a plenum chamber and at least three access ports to said plenum chamber, said foldable housing being defined by a cross-limb and a transabdominal limb joined to one another in a T-configuration and said limbs together defining an articular joint; and an elongated, flexible, fluted, virgate liquid transport segment received in and extending outwardly from each of two of said access ports;

said fluted, virgate segment defining plural liquid transport channels along the longitudinal axis of each segment.

2. A catheter suitable for peritoneal dialysis and comprising a resilient, foldable housing defining a plenum chamber and at least three access ports to said plenum chamber; and an elongated, flexible, fluted, virgate liquid transport segment received in and extending outwardly from each of two of said access ports while opposite ends of the fluted segment are received in two of said access ports;

said fluted, virgate segment defining plural liquid transport channels along the longitudinal axis of each segment.

3. A catheter suitable for peritoneal dialysis and comprising a resilient, foldable housing defining a plenum chamber and at least three access ports to said plenum chamber; and two separate fluted segments received in two of said access ports;

said fluted, virgate segment defining plural liquid transport channels along the longitudinal axis of each segment.

4. The catheter in accordance with claim 3 wherein said foldable housing has a Y-configuration.

5. The catheter in accordance with claim 3 wherein said foldable housing is provided with a septum that partitions the plenum chamber into two portions and wherein each of the two portions has a pair of access ports.

6. The catheter in accordance with claim 3 wherein the fluted segments have a substantially cylindrical transverse cross-section.

7. The catheter in accordance with claim 3 wherein the fluted segments have an oblong transverse cross-section.

8. The catheter in accordance with claim 3 wherein said resilient, foldable housing is defined by a hollow cross limb joined to a hollow transabdominal limb, and wherein the hollow transabdominal limb is arcuate.

9. The catheter in accordance with claim 3 wherein said resilient foldable housing is defined by a hollow cross-limb joined to a hollow transabdominal limb, and wherein the transabdominal limb includes an arcuate portion of about $\pi/2$ radians and having a substantially constant radius of curvature.

10. A catheter suitable for peritoneal dialysis and comprising a resilient, foldable housing defining a plenum chamber and at least three access ports to said plenum chamber; and an elongated, flexible, fluted, virgate liquid transport segment received in and extending outwardly from each of two of said access ports;

said fluted, virgate segment defining plural liquid transport channels along the longitudinal axis of each segment; said foldable housing being provided with a septum that partitions the plenum chamber into two portions, each of the two portions being provided with a pair of access ports, and one said fluted strip segment being received in and extending outwardly from an access port in each said portion of the plenum chamber.

11. A catheter suitable for peritoneal dialysis and comprising a resilient, foldable housing defining a plenum chamber and at least three access ports to said plenum chamber; and an elongated, flexible, fluted, virgate liquid transport segment received in and extending outwardly from each of two of said access ports;

each said fluted, virgate segment defining plural liquid transport channels along the longitudinal axis of each segment, and said fluted strip segment being connected to one another in said plenum chamber.

* * * * *